United States Patent [19]

Linde et al.

[11] Patent Number: 4,566,112
[45] Date of Patent: Jan. 21, 1986

[54] TOMOSYNTHESIS APPARATUS

[75] Inventors: Rolf Linde, Haseldorf; Erhard Klotz, Halstenbek, both of Fed. Rep. of Germany

[73] Assignee: U.S. Philips Corporation, New York, N.Y.

[21] Appl. No.: 580,763

[22] Filed: Feb. 17, 1984

Related U.S. Application Data

[63] Continuation of Ser. No. 378,573, May 17, 1982, abandoned.

[30] Foreign Application Priority Data

May 29, 1981 [DE] Fed. Rep. of Germany ....... 3121324

[51] Int. Cl.⁴ .............................................. G03B 41/16
[52] U.S. Cl. ........................................... 378/2; 378/23
[58] Field of Search ...................... 378/2, 23

[56] References Cited

U.S. PATENT DOCUMENTS 4,132,896 1/1979 Klotz ........................................ 378/2
4,416,019 11/1983 Weiss ...................................... 378/2

FOREIGN PATENT DOCUMENTS 2035769 6/1980 United Kingdom ................... 378/2

Primary Examiner—Craig E. Church
Attorney, Agent, or Firm—Marc D. Schechter

[57] ABSTRACT

A tomosynthesis apparatus for the formation of layer images of a body. The apparatus has a large number of radiation source positions which are situated in one radiation source plane. The radiation from the sources in stopped by a diaphragm device so that the radiation beams passing through the diaphragm apertures irradiate a common superposition zone and are incident on a detector surface which is arranged behind the superposition zone. The diaphragm apertures are shaped so that in the detector plane the edge of the radiation beam of each radiation source is at least locally tangent to the edge of a cylinder which is centrally projected onto the detector surface by the radiation source and which is situated within the superposition zone. The axis of the cylinder extends at least approximately perpendicular to the radiation source plane.

6 Claims, 3 Drawing Figures

TOMOSYNTHESIS APPARATUS

This is a continuation of application Ser. No. 378,573, filed May 17, 1982, now abandoned.

BACKGROUND OF THE INVENTION

The invention relates to a tomosynthesis apparatus for the formation of layer images of a body. The apparatus has a large number of radiation source positions which are situated in one radiation source plane, a diaphragm device for forming radiation beams which irradiate a common superposition zone, and a detector which is situated in a detector plane behind the superposition zone.

An apparatus of this kind is known from United Kingdom Patent Application No. 2,035,769 (corresponding to German Offenlegungsschrift No. 2847011). The radiation beams are formed by means of diaphragm apertures so that the beams, having substantially equally large beam cross-sections, register in a predetermined superposition plane. As the distance from the superposition plane increases, the common superposition zone of the radiation beams becomes tapered. The radiation beams themselves are recorded as a superposition image on the detector surface in a more or less superposed form.

The formation of layer images of a body, which images are situated within the superposition zone, is realized by imaging the superposition image on a light-sensitive layer, for example a frosted glass plate, by means of an imaging matrix. The imaging matrix may be for example, a lens matrix whose imaging elements or lenses are arranged in the matrix plane according to with the flat distribution of the radiation sources. By displacement of the light-sensitive layer or the imaging matrix in the direction of the optical axis with respect to the detector surface, different layers of the superposition zone within the body can be imaged on the light-sensitive layer. The body layer within the superposition zone is then optimally reconstructed, while the images of the body layers situated above or below the reconstructed layer have a reduced image quality due to the decreasing degree of superposition of the radiation beams.

It is often desirable to image cylindrical body zones whose cylinder axes extend substantially perpendicularly to the radiation source plane by means of such a continuous slice imaging process (that is to say by means of a process which images a large number of approximately equally large layers the images being of substantially the same image quality, and which layers are situated behind one another, viewed in the direction of the cylinder axis). However, such a cylindrical zone can be situated only within the superposition zone. In the superposition plane of all radiation beams, the size of the superposition zone is substantially larger than the corresponding dimension of the cylindrical zone.

Therefore, for the layer imaging of a cylindrical body zone in the known apparatus, a substantially large zone of the body is irradiated in addition to the area claimed to be imaged. This has an adverse effect on the radiation load for the body as well as on the quality of the layer images, because a larger amount of scatter radiation is produced, and hence more artefacts appear in the layer images due to the comparatively strong superposition of the radiation beams on the detector surface.

SUMMARY OF THE INVENTION

It is an object of the invention to provide a tomosynthesis apparatus for the formation of layer images of a body which is suitable for the continuous layer imaging of cylindrical body zones, and which a reduced radiation load supplies to the body. Layer images of higher quality can be obtained with such a device.

This object is achieved according to the invention in that diaphragm apertures of the diaphragm device are shaped and oriented so that edge rays of the radiation beam of each radiation source are tangent to boundaries of a cylinder. The cylinder has a cylinder axis which is directed transverse to the detector surface and which is situated within the superposition zone.

The cylinders are assumed to be circular cylinders which are situated within the superposition zone or cylinders whose cross-sections perpendicular to the cylinder axis are rectangular, square or otherwise shaped. The diaphragm apertures are so large that at least some of the edge rays of each radiation beam are tangent to the cylinder.

Due to this bounding of all radiation beams to the cylinder, only a minimum additional body volume outside the cylindrical zone is irradiated in comparison with the state of the art, so that the radiation load for the body decreases. Because a smaller total body volume is irradiated by the radiation beams, less scattered radiation is produced, so that the apparatus produces layer images with a higher contrast. Due to the reduction of the angle of aperture of the radiation beams, a more uniform degree of superposition of the radiation beams in the direction of the cylinder axis is achieved, so that layer images of the same image quality are obtained. Moreover, the radiation beams or the perspective images of the body formed thereby are not superposed on the detector plane to the same high degree as in the known apparatus, so that the artefacts in the layer images are reduced.

DESCRIPTION OF THE PREFERRED EMBODIMENTS

Figure 1:
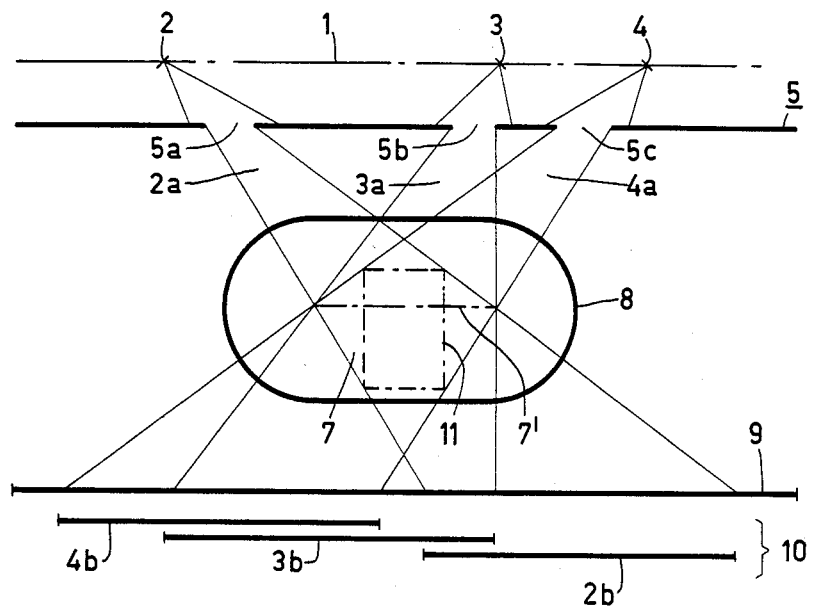
FIG. 1 shows a known tomosynthesis apparatus for the formation of superposition images of a body.

The known apparatus which is shown in FIG. 1 comprises several radiation sources 2, 3, and 4, which are for example, X-ray tubes in a common tank. The sources can be simultaneously briefly flashed, and they are arranged in a radiation source plane 1.

The radiation of the sources is stopped to form radiation beams 2a, 3a, and 4a by means of equally large apertures 5a, 5b, and 5c in a diaphragm plate 5. The radiation beams irradiate a common zone 7 (a superposition zone) which is situated within a body 8 to be examined. All cross-sections of the beams 2a, 3a, and 4a which are situated within a superposition plane 7' substantially register.

The perspective images 2b, 3b, and 4b of the body 8 obtained by means of the radiation beams 2a, 3a, and 4a are recorded in superposed form as a superposition image 10 on a detector surface 9 which is situated underneath the body 8. For the sake of clarity, FIG. 1 separately shows the perspective images 2b, 3b, 4b, underneath the detector surface 9 which may be, for example, an X-ray film.

For forming images of layers of the body 8 which are situated within the superposition zone 7 and in which an imaginary cylinder 11 can be inscribed, the superposition image 10 is imaged in known manner on a recording surface by means of an imaging matrix. To this end the recording surface (for example, a frosted glass plate) as well as the imaging matrix (not shown) can be displaced perpendicularly to the radiation source plane with respect to the superposition image, so that different layer images of the object can be reproduced.

Figure 2:
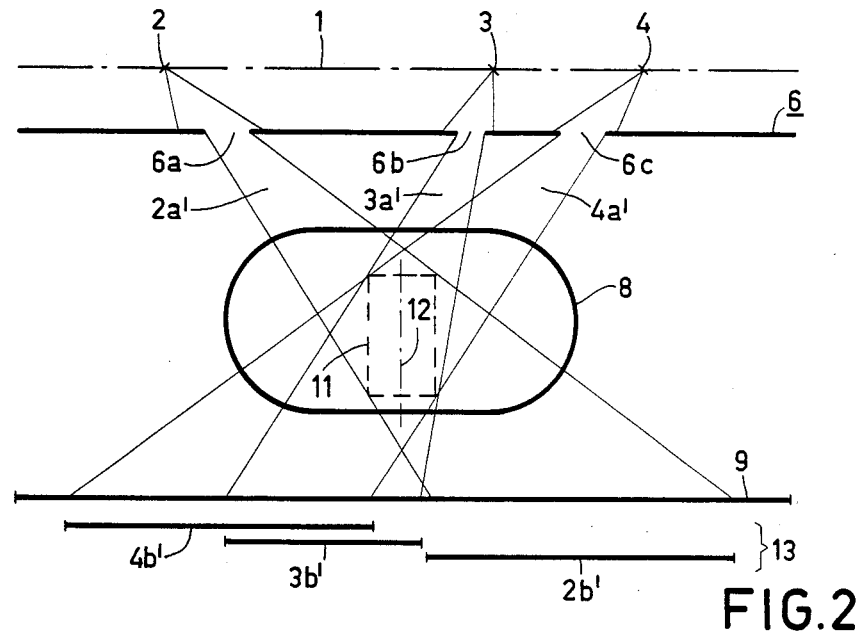
FIG. 2 shows a tomosynthesis apparatus according to the invention.

In the tomosynthesis apparatus according to the invention which is shown in FIG. 2, the X-rays emitted by the radiation sources 2, 3, and 4 are stopped by means of diaphragm apertures 6a, 6b, and 6c in a diaphragm device 6 so that the radiation beams 2a', 3a', and 4a' irradiate only the imaginary cylindrical zone 11 of FIG. 1 which is situated within the superposition zone 7 of the known apparatus. Cylinder axis 12 of cylinder 11 extends perpendicularly to the radiation source plane 1. The diaphragm apertures 6a, 6b, and 6c are shaped and oriented so that the radiation beam edge situated in the detector plane 9 is at least locally tangent to the boundary of the projection of the cylinder onto the detector surface by the relevant radiation source.

The perspective image 13 consists of the perspective images 2b', 3b', and 4b' associated with the radiation beam 6a to 6c. It is again shown underneath the detector 9 for the sake of clarity. As has already been described with reference to FIG. 1, layer images which are situated within the cylinder 11 are formed therefrom, for example, by means of the already described imaging matrix and frosted glass plate.

A comparison of the two devices shown in FIGS. 1 and 2 reveals that during the irradiation or the layerwise imaging of this cylindrical zone 11, the perspective images 2b' to 4b' are superposed to a substantially smaller degree than the perspective images 2b to 4b of the known apparatus. Consequently, the apparatus shown in FIG. 2 produces layer images containing fewer artefacts. Furthermore, a smaller body volume is irradiated in comparison with the known apparatus, so that the radiation load for the body 8 is reduced or the contrast of the layer images is increased, because less scattered radiation is produced during the irradiation of a smaller body volume.

In a further embodiment according to the invention, the diaphragm apertures 6a, 6b, and 6c in the diaphragm device 6 can be shaped so that the edges of the radiation beams and those of the associated projection cross-sections of the cylinder register on the detector surface. It is thus achieved that the radiation beams 2a', 3a', and 4a' are concentrated even more on the cylindrical zone.

Figure 3:
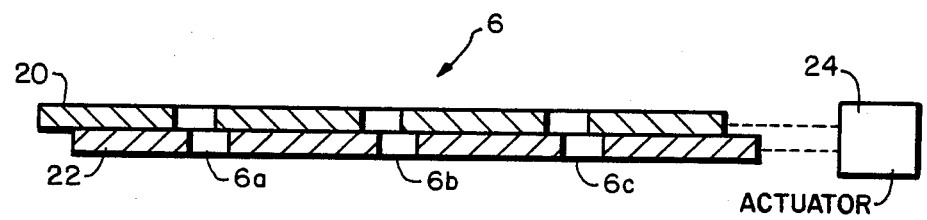
FIG. 3 is a partly cross-sectional, partly schematic illustration of a diaphragm device for use in a tomosynthesis apparatus according to the invention.

The diaphragm device 6 (FIG. 2) preferably consists of a diaphragm plate comprising fixed diaphragm apertures 6a, 6b, and 6c. The diaphragm device 6, however, may alternately comprise displaceable or adjustable diaphragm apertures 6a, 6b, and 6c for adaptation to cylindrical zones 11 of different size. (FIG. 3.) The adjustable diaphragm device 6 shown in FIG. 3 includes two diaphragm plates 20 and 22 moveable by an actuator 24 in the directions of the broken lines. Alternatively a set of exchangeable diaphragm plates comprising fixed diaphragm apertures of different size can be used.

Obviously, the tomosynthesis apparatus according to invention as shown in FIG. 2 can also be used for recording spatial-raster coded superposition images, for example, as known from U.S. Pat. No. 4,145,614 to Kowalski (corresponding to German Auslegeschrift No. 2546785).

What is claimed is:

1. A tomosynthesis apparatus for forming images of layers of a body, said apparatus comprising:
    at least one radiation source for irradiating the body from a plurality of radiation source positions, said radiation source positions being situated in a radiation source plane on a first side of the body;
    a diaphragm device positioned on the first side of the body between the radiation source plane and the body, said diaphragm having apertures therein for forming radiation beams which irradiate a common zone of the body; and
    a detector in a detector plane located on a second side of the body opposite the first side;
    characterized in that the apertures in the diaphragm are shaped and oriented such that the radiation beams formed therefrom have edge rays at the periphery of each beam, the edge rays being tangent to the boundaries of a cylinder situated within the common zone of the body, said cylinder having an axis transverse to the detector plane.

2. A tomosynthesis apparatus as claimed in claim 1, characterized in that the diaphragm device comprises a diaphragm plate having displaceable diaphragm apertures.

3. A tomosynthesis apparatus as claimed in claim 1, characterized in that the diaphragm device comprises a diaphragm plate having adjustable diaphragm apertures.

4. A tomosynthesis apparatus as claimed in claim 1, characterized in that the apertures in the diaphragm are shaped such that for each radiation beam, the edge rays of the radiation beam coincide in the detector plane with a projection of the cylinder in the detector plane, said coinciding projection formed by the source of the associated radiation beam.

5. A tomosynthesis apparatus as claimed in claim 4, characterized in that the diaphragm device comprises a diaphragm plate having displaceable diaphragm apertures.

6. A tomosynthesis apparatus as claimed in claim 4, characterized in that the diaphragm device comprises a diaphragm plate having adjustable diaphragm apertures.

* * * * *